United States Patent [19]

Gin et al.

[11] Patent Number: 5,006,310
[45] Date of Patent: Apr. 9, 1991

[54] SCHIRMER TEAR TEST

[75] Inventors: Jerry Gin, Sunnyvale, Calif.; Vernon G. Wong, Rockville, Md.

[73] Assignee: Visionex, Sunnyvale, Calif.

[21] Appl. No.: 431,522

[22] Filed: Nov. 3, 1989

[51] Int. Cl.$^5$ ............................................. G01N 31/22
[52] U.S. Cl. ........................................ 422/56; 422/57; 422/58; 435/805; 436/162; 436/169
[58] Field of Search ................... 422/56, 57, 58, 82.05; 435/805; 436/162, 169

[56] References Cited

U.S. PATENT DOCUMENTS

| | | | |
|---|---|---|---|
| 3,420,205 | 1/1969 | Morison | 422/56 |
| 3,819,490 | 6/1974 | Klingstrom et al. | 435/32 |
| 4,095,950 | 6/1978 | Kahn | 436/161 |
| 4,428,908 | 1/1984 | Ashley et al. | 422/56 |
| 4,857,453 | 8/1989 | Ullman et al. | 435/805 |

OTHER PUBLICATIONS

Gifford, Sanford R., et al., "Keratoconjuctivitis Sicca" in *Archives of Ophthalmology* (1943) 30: 207–216.
Jones, L. T. and Linn, M. L., "The Diagnosis of the Causes of Epiphora" in *American Journal of Ophthamology* (May 1969) pp. 751–754.
Roth, Andrew de, "Hypofunction of the Lacrimal Gland" from the Department of Ophthamology, Northwestern University Medical School. Read before the Chicago Ophthamological Society (Mar. 1940).

*Primary Examiner*—Robert J. Warden
*Assistant Examiner*—Jill Johnston
*Attorney, Agent, or Firm*—Bertram I. Rowland

[57] ABSTRACT

An improved Schirmer I Tear Test is provided. The improvement comprises a strip having a graduated migration scale printed on the test strip and the presence of a water soluble marker dye that comigrates with the tear migration front. Both improvements serve to increase the reproducibility of the test and ease which with the results are read.

5 Claims, No Drawings

SCHIRMER TEAR TEST

TECHNICAL FIELD

The subject invention is in the field of ophthalmic disease diagnosis.

BACKGROUND

The ability to quantitatively measure tear production is important for the diagnosis of many types of lacrimal dysfunction. Patients may experience either excessive tear formation (epiphora) or decreased tear production, such as keratoconjunctivitis sicca (associated with Sjögren syndrome). The measurement of tear production levels is also important for determining if a patient is a good candidate for contact lenses.

Quantitative measurement of tear production has traditionally been measured by a Schirmer I Tear Test. The standardized Schirmer I Tear Test consists of a 5×35 mm strip of Whatman #41 filter paper; the paper has a notch located 5 mm from one end of the strip. The notched end of the strip is rounded.

The Schirmer Tear Test is performed as follows. The test strip is bent at the notch (~120° bend). The rounded end of the Schirmer I Tear Test strip is then inserted into the lower conjunctival sac of each eye. The eyes are then closed. The strip is progressively wetted by capillary action drawing up tears as they are produced. The distance the tear migration front has moved is measured after 5 minutes. The migration distance of the tears is measured from the notch of the strip as the zero point. Reading the test involves removing the strip from the eye and placing it against a scale graduated in millimeters. 15 mm of wetting in 5 minutes is considered normal. It is imperative that the tear migration front be measured as close to the 5 minute time mark as possible because the tear front will continue to migrate up the strip after the strip is removed from the eye. Thus, late readings give rise to results that are artificially high.

Relevant Literature

Background information describing the diagnostic use of the conventional Schirmer I Tear Test is given in the following articles: Gifford et al., *Archives of Ophthalmology* (1943) 30:207-216; Jones et al., *American Journal of Ophthalmology* (1969) 5:751-754; A. De Rotth *American Journal of Ophthalmology* (1941) 24:20-25.

SUMMARY OF THE INVENTION

The subject invention provides for an improved version of the Schirmer I Tear Test. The improvement consists of both a tear migration front scale printed on the test strip, and a water soluble marker dye that facilitates visualization of the tear migration front. Both improvements serve to increase the reproducibility and ease with which the test results are read.

DESCRIPTION OF SPECIFIC EMBODIMENTS

Improved versions of the Schirmer I Tear Test are provided. The improvements of the test serve to increase the reproducibility and ease of reading the test results. One of the improvements in the test consists of a tear migration front scale printed directly on the test strip. A second improvement consists of including a marking dye on the test strip so as to facilitate the visualization of the tear migration front.

The shape and material of the filter paper component of the improved Schirmer I Tear Test is essentially the same as the conventional Schirmer I Test. The improved Schirmer I Tear Test may be made from any type of filter paper currently used to manufacture conventional Schirmer I Tear Tests. Suitable filter material must be able to absorb tears by capillary action. Filter paper used for the manufacture of the Schirmer Test will usually be ashless, non-hardened, analytical filter paper having flow characteristics similar to Whatman #41 filter paper. Preferably, Schirmer I Tear Test strips are made from Whatman #41 filter paper.

The shape of the subject improved Schirmer I Tear Test is essentially the same size and shape as conventional Schirmer I Tear Tests. The strip is about 5×35 mm in size. The strip is rounded on one end and a notch will be present about 5 mm from the rounded end of the test strip. The shape of the notch is not essential to the performance of the test. The notch is usually a 90° cut, placed such that the apex of the notch does not protrude past a median longitudinal axis of the test strip.

The subject Schirmer I Tear Test contains a printed graduated scale that allows one to rapidly and accurately measure the tear migration front without referring to a printed scale separate from the strip. The ink used for the printed scale is substantially water insoluble. The ink may be of any single color or of multiple colors. Preferably, the ink is of a single dark color. Conveniently, the ink will be black. The scale may be printed either on a single side, or both sides of the test strip for easier extrapolation where the front is not normal to the sides of the strip.

The printed scale is in uniformly graduated in units, the normal unit being millimeters. The scale is arranged so that the distance the tear migration front travels from the conjunctival sac is conveniently measured. The low end of the scale is closest to the notched end of the strip. The scale consists of gradation lines marked with numbers so as to indicate the migration distance. Not every line need be marked with a number. In addition to the quantitative markings on the scale, the scale may also contain qualitative markings that indicate critical result ranges, e.g., a special mark indicating the tear migration distance in a normal individual.

The subject Schirmer I Tear Test also comprise a water soluble dye designed to aid visualization of the tear migration front. Suitable dyes have a migration front essentially coincident with the tear migration front. Suitable dyes are non-toxic, particularly those dyes have Federal Food and Drug Commission approval. FD&C Blue Dye No. 1 is exemplary, but not exclusive of dyes that may be used in the subject Schirmer I Tear Test. The dye is diffusibly present on the test strip prior to the use of the strip. Conveniently, the dye may be present as a linear or circular spot located near the zero point of the printed scale, proximal to the portion of the strip introduced into the conjunctival sac. The surface area of dye spot will be a small fraction of the surface area of the subject Schirmer test strip, preferably less than 5% of the surface area, more preferably less than 1% of the surface area.

The dye may be applied to the test strip in a variety of ways. The method of application of the dye to the test strip during manufacture is not important to the function of the test strip. Exemplary, but not exclusive of methods for applying the dye to the test strip is impact printing. The dye may be printed on either a single side or both sides of the test strip.

The subject Schirmer I Tear Test strip is maintained sterile prior to its use. The method of achieving sterilization is conventional. Exemplary, but not exclusive of methods of sterilization, is sterilization by ionizing radiation. The sterilized subject Schirmer I Test strip is stored in a pouch capable of maintaining the sterility of the test prior to use.

With the exception of the method by which the subject test results are read, the subject Schirmer I Test is performed essentially as the conventional Schirmer I Tear Test. The test is essentially performed as follows: While still in the sterile pouch, the Schirmer I Tear Test strip is bent at the notch. The sterile pouch is then opened and the rounded end of the test strip is inserted in the lower conjunctival sac near the outer angle, being careful not to touch the cornea. The eyes are then closed for 5 minutes. At the end of 5 minutes, the distance the dye front has migrated is noted. The test need not be removed from the eye in order to be read as is presently performed.

The subject test strip provides many advantages of convenience, ease of reading, increased accuracy and reduced likelihood of erroneous results. Experience obtained with the conventional Schirmer I Test strip is readily applicable in that new procedures are not required.

All publications cited in this specification are herein incorporated by reference as if each individual publication or patent application were specifically and individually indicated to be incorporated by reference.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. In a Schirmer Tear Test strip, the improvement comprising a graduated scale index printed on said strip for measuring the migration distance of the tear migration front, wherein said scale index is printed in essentially water insoluble ink, and
   a water soluble dye that essentially co-migrates with the tear migration front positioned proximal to the end of said strip for insertion into the conjunctival sac of the eye.

2. A strip according to claim 1 wherein said graduated scale index has lines graduated in millimeters.

3. A strip according to claim 1 wherein said dye is FD&C Blue No. 1.

4. A strip according to claim 1, whereas said strip is Whatman #41 paper.

5. In a Schrimer Tear Test strip, the improvement comprising: a graduated millimeter scale index having line gradations printed along at least one side of said strip; and
   a spot of FD&C Blue Dye No. 1 proximal to the end of said strip for insertion into the conjunctival sac of the eye.

* * * * *